United States Patent [19]

Schotland

[11] Patent Number: 5,758,653

[45] Date of Patent: Jun. 2, 1998

[54] SIMULTANEOUS ABSORPTION AND DIFFUSION IMAGING SYSTEM AND METHOD USING DIRECT RECONSTRUCTION OF SCATTERED RADIATION

[75] Inventor: John Carl Schotland, Wynnewood, Pa.

[73] Assignee: Bell Communications Research, Inc., Morristown, N.J.

[21] Appl. No.: 419,686

[22] Filed: Apr. 10, 1995

[51] Int. Cl.$^6$ .................................................. A61B 6/00
[52] U.S. Cl. .................... 128/665; 128/633; 128/653.1; 356/340; 356/432; 250/574
[58] Field of Search .................... 128/653.1, 664, 128/665, 633; 356/303, 326, 432, 433, 318, 328; 250/574

[56] References Cited

U.S. PATENT DOCUMENTS

| | | | |
|---|---|---|---|
| 5,032,024 | 7/1991 | Cope | 128/633 |
| 5,070,455 | 12/1991 | Singer et al. | 364/413.19 |
| 5,203,339 | 4/1993 | Knuttel et al. | 128/665 |
| 5,213,105 | 5/1993 | Gratton et al. | 128/252 |
| 5,349,951 | 9/1994 | Ito et al. | 128/665 |
| 5,371,368 | 12/1994 | Alfano et al. | 128/664 |
| 5,386,827 | 2/1995 | Chance et al. | 128/665 |
| 5,413,098 | 5/1995 | Benaron | 128/665 |
| 5,492,118 | 2/1996 | Gratton et al. | 128/664 |
| 5,528,365 | 6/1996 | Gonatas | 128/665 |

*Primary Examiner*—Brian L. Casler
*Attorney, Agent, or Firm*—Joseph Giordano; Loria B. Yeadon; James W. Falk

[57] ABSTRACT

A method for the direct reconstruction of the absorption and diffusion images from measurements of the transmitted intensity of the scattered radiation effected by irradiating the object with a time-domain source. The transmitted intensity is related to the absorption and the diffusion coefficients by an integral operator. The images are directly reconstructed by executing a prescribed mathematical algorithm, as determined with reference to the integral operator, on the transmitted intensity.

4 Claims, 9 Drawing Sheets

(i)

(ii)

SIMULTANEOUS ABSORPTION AND DIFFUSION IMAGING SYSTEM AND METHOD USING DIRECT RECONSTRUCTION OF SCATTERED RADIATION

FIELD OF THE INVENTION

This invention relates generally to a system, and concomitant methodology, for generating diffusion images of an object and, more particularly, to such system and methodology for which the image is directly reconstructed from measurements of scattered radiation detected by irradiating the object with a time domain source.

BACKGROUND OF THE INVENTION

The inventive subject matter addresses the physical principles and the associated mathematical formulations underlying the direct reconstruction method for optical imaging in the multiple scattering regime. The result is a methodology for the direct solution to the image reconstruction problem. Moreover, the method is generally applicable to imaging with any scalar wave in the diffusive multiple scattering regime and is not limited to optical imaging. However, for the sake of elucidating the significant ramifications of the present invention, it is most instructive to select one area of application of the method so as to insure a measure of definiteness and concreteness to the description. Accordingly, since many biological systems meet the physical requirements for the application of the principles of the present invention, especially photon diffusion imaging principles, the fundamental aspects of the present inventive subject matter will be conveyed using medical imaging as an illustrative application of the method.

There have been three major developments in medical imaging over the past 20 years that have aided in the diagnosis and treatment of numerous medical conditions, particularly as applied to the human anatomy; these developments are: (1) the Computer-Assisted Tomography (CAT) scan; (2) the Magnetic Resonance Imaging (MRI); and (3) the Positron Emission Tomography (PET) scan.

With a CAT scanner, X-rays are transmitted through, for example, a human brain, and a computer uses X-rays detected external to the human head to create and display a series of images—basically cross-sections of the human brain. What is being imaged is the X-ray absorption coefficient for unscattered, hard X-rays within the brain. CAT scans can detect, for instance, strokes, tumors, and cancers. With an MRI device, a computer processes data from radio signals impinging on the brain to assemble life-like, three-dimensional images. As with a CAT scan, such malformations as tumors, blood clots, and atrophied regions can be detected. With a PET scanner, the positions of an injected radioactive substance are detected and imaged as the brain uses the substance. What is being imaged is the gamma ray source position. Each of these medical imaging techniques has proved invaluable to the detection and diagnosing of many abnormal medical conditions. However, in many respects, none of the techniques is completely satisfactory for the reasons indicated in the following discussion.

In establishing optimal design parameters for a medical imaging technique, the following four specifications are most important. The specifications are briefly presented in overview fashion before a more detailed discussion is provided; moreover, the shortcomings of each of the conventional techniques are also outlined. First, it would be preferable to use a non-ionizing source of radiation. Second, it would be advantageous to achieve spatial resolution on the order of a millimeter to facilitate diagnosis. Third, it would be desirable to obtain metabolic information. And, fourth, it would be beneficial to produce imaging information in essentially real-time (on the order of one millisecond) so that moving picture-like images could be viewed. None of the three conventional imaging techniques is capable of achieving all four specifications at once. For instance, a CAT scanner is capable of high resolution, but it uses ionizing radiation, it is not capable of metabolic imaging, and its spatial resolution is borderline acceptable. Also, while MRI does use non-ionizing radiation and has acceptable resolution, MRI does not provide metabolic information and is not particularly fast. Finally, a PET scanner does provide metabolic information, but PET uses ionizing radiation, is slow, and spatial resolution is also borderline acceptable. Moreover, the PET technique is invasive due to the injected substance.

The four specifications are now considered in more detail. With respect to ionizing radiation, a good deal of controversy as to its effects on the human body presently exists in the medical community. To ensure that the radiation levels are within what are now believed to be acceptable limits, PET scans cannot be performed at close time intervals (oftentimes, it is necessary to wait at least 6 months between scans), and the dosage must be regulated. Moreover, PET is still a research tool because a cyclotron is needed to make the positron-emitting isotopes. Regarding spatial resolution, it is somewhat self-evident that diagnosis will be difficult without the necessary granularity to differentiate different structures as well as undesired conditions such as blood clots or tumors. With regard to metabolic information, it would be desirable, for example, to make a spatial map of oxygen concentration in the human head, or a spatial map of glucose concentration in the brain. The ability to generate such maps can teach medical personnel about disease as well as normal functions. Unfortunately, CAT and MRI report density measurements—electrons in an X-ray scanner or protons in MRI—and there is not a great deal of contrast to ascertain metabolic information, that is, it is virtually impossible to distinguish one chemical (such as glucose) from another. PET scanners have the ability to obtain metabolic information, which suggests the reason for the recent popularity of this technique. Finally, imaging is accomplished only after a substantial processing time, so real-time imaging is virtually impossible with the conventional techniques.

Because of the aforementioned difficulties and limitations, there has been much current interest in the development of a technique for generating images of the distribution of photon diffusion and absorption coefficients of living tissue that satisfy the foregoing four desiderata. Accordingly, a technique using low intensity photons would be safe. The technique should be fast in that optical events occur within the range of 10 nanoseconds—with this speed, numerous measurements could be completed and averaged to reduce measurement noise while still achieving the one millisecond speed for real-time imaging. In addition, source and detector equipment for the technique may be arranged to produce necessary measurement data for a reconstruction procedure utilizing appropriately-selected spatial parameters to thereby yield the desired one millimeter spatial resolution. Finally, metabolic imaging with the technique should be realizable if imaging as localized spectroscopy is envisioned in the sense that each point in the image is assigned an absorption spectrum. Such an assignment may be used, for example, to make a map of oxygenation by measuring the absorption spectra for hemoglobin at two different wavelengths, namely, a first wavelength at which hemoglobin is saturated, and a second wavelength at which hemoglobin is de-saturated. The difference of the measurements can yield a hemoglobin saturation map which can, in turn, give rise to tissue oxygenation information.

The first proposals for optical imaging suggested a mathematical approach (e.g., backprojection algorithm) that is similar to that used to generate X-ray computerized tomography images. Light from a pulsed laser is incident on the specimen at a source position and is detected at a detector strategically placed at a point to receive transmitted photons. It is assumed that the earliest arriving photons (the so-called "ballistic photons") travel in a straight line between the source and detector, and the transmitted intensity is used in a mathematical reconstruction algorithm. In effect, only unscattered incident waves are considered as being useful for forming an image of any objects embedded in the specimen and, accordingly, techniques are employed to eliminate scattered light from the detection process, such as arranging a detector with "fast gating time" to only process the earliest arriving photons. However, since it is known that the ballistic photons are attenuated exponentially, if the specimen has a thickness exceeding a predetermined value, imaging is virtually impossible in many practical situations.

The latest proposals for optical imaging are now directed toward imaging systems which use scattered and diffused radiation to reconstruct a representation of the interior of a specimen. Representative of prior art in this field is U.S. Pat. No. 5,070,455 issued to Singer et al (Singer) on Dec. 3, 1991. The system disclosed by Singer uses radiation, such as photons or other particles, which will be scattered to a significant degree by the internal structure of a specimen. In the system, a specimen is irradiated and measurements of the attenuated and scattered radiation are effected at a number of points along the exterior of the specimen. It has been determined by Singer that such measurements are sufficient to determine the scattering and attenuation properties of the various regions inside the specimen. In accordance with the disclosure of Singer, the interior of the specimen is modeled as an array of volume elements ("voxels"). Each voxel in the model of the specimen has scattering and attenuation properties which are represented by numerical parameters that can be mapped so as to generate several images of the interior of the specimen.

The particular technique used by Singer to reconstruct the interior of the specimen can best be characterized as an "iterative" procedure. This procedure is now described in some detail so as to pinpoint its shortcomings and deficiencies. After collecting the imaging data, the scattering and attenuation coefficients for the voxels are assigned initial values, which helps to shorten the computation process—but which is also the characteristic of iterative or non-direct solution to a mathematical minimization problem. Next, the system computes the intensity of light that would emerge from the specimen if the interior of the object were characterized by the currently assigned values for the scattering and attenuation coefficients. Then, the difference between the measured light intensities and the computed light intensities are used to compute an "error function" related to the magnitude of the errors of reconstruction. This error function (also called "cost function" in minimization procedures) is then minimized using a multi-dimensional gradient descent methodology (such as Fletcher-Powell minimization), i.e., the coefficients are modified so as to reduce the value of the error function.

The process of computing exiting light intensities based on the currently assigned values for the scattering and attenuation coefficients, and then comparing the differences between the computed values and measured values to generate a new approximation of the scattering and attenuation properties of the interior of the specimen, continues until the error function falls below a specified threshold. The final values of the scattering and attenuation coefficients from this process are then mapped so as to generate a series of images of the interior of the specimen, thereby depicting the attenuation and scattering characteristics of the specimen's interior—which presumably will disclose both normal and abnormal conditions.

Singer thus discloses a technique to reconstruct an image by inversion using an iterative minimization procedure. Such an approach is more formally characterized as a "heuristic", in contrast to an "algorithm", since no verification or proof of even the existence of a solution using the approach has been offered. There are essentially an infinite number of scattering and attenuation coefficients under such a regime, and there is absolutely no assurance that the particular coefficients determined using the iterative technique are the actual coefficients for the specimen's interior. Moreover, such a heuristic method has a high computational complexity which is exponential in relation to the number of voxels and which is, in turn, a characteristic of difficult optimization problems with many local minima. The computational complexity of such a approach renders the reconstruction method virtually useless for imaging.

The other approaches presented in the prior art are closely related to that presented by Singer. These approaches also effect an indirect inversion of the forward scattering problem by an iterative technique which provide little, if any, physical insight.

SUMMARY OF THE INVENTION

These limitations and other shortcomings and deficiencies of conventional techniques are obviated, in accordance with the present invention, by utilizing a direct reconstruction methodology, and concomitant system, to generate images of an object under investigation; the direct reconstruction formulation guarantees both the existence and uniqueness of the imaging technique. Moreover, the direct reconstruction method significantly reduces computational complexity.

In accordance with the broad aspect of the present invention, the object under study is irradiated by a time-domain source and the transmitted intensity due predominantly to diffusively scattered radiation is measured at selected locations proximate to the object wherein the transmitted intensity is related to both the absorption and the diffusion coefficients by an integral operator. The absorption and diffusion images of the object are directly reconstructed by executing a prescribed mathematical algorithm, determined with reference to the integral operator, on the transmitted intensity measurements. In addition, radiation at different wavelengths effects imaging as localized spectroscopy.

The organization and operation of this invention will be understood from a consideration of the detailed description of the illustrative embodiment, which follows, when taken in conjunction with the accompanying drawing.

BRIEF DESCRIPTION OF THE DRAWING

The same element appearing in more than one FIG. has the same reference numeral.

DETAILED DESCRIPTION

To place in perspective the detailed description of the present invention and thereby highlight the departure from the art as disclosed and claimed herein, it is both instructive and informative to first gain a basic understanding of the imaging environment in which the present invention operates by presenting certain foundational principles pertaining to the subject matter in accordance with the present invention. Accordingly, the first part of the description focuses on a high-level discussion of the imaging systems relevant to the inventive subject matter; this approach has the advantage of introducing notation and terminology which will aid in elucidating the various detailed aspects of the present invention. After this overview, the system aspects of the present invention, as well as the concomitant methodology, are presented with specificity.

Overview of the Present Invention

Multiple scattering of light presents a fundamental physical obstruction to optical imaging. The inventive subject matter of the present invention addresses this phenomena, with the surprising result that diffusive light contains sufficient information to image the optical diffusion of a highly scattering medium. This conclusion obtains from an integral equation formulation of inverse scattering theory that is applicable to multiple scattering in the diffusion limit. Using this representation, the first direct reconstruction procedure ever devised for imaging the optical diffusion and absorption coefficients of a highly scattering medium is elucidated. In contrast to techniques which utilize unscattered (ballistic) photons for image formation, the procedure in accordance with the present invention allows for the imaging of objects whose size is large compared to the average scattering mean free path.

The familiar opaque or cloudy appearance of many objects having impinging light may be explained by the phenomenon of multiple light scattering. (It is to be noted that terminology will be generalized hereinafter so that an "object" is the physical manifestation of what is under study—such an object may stand alone, may be embedded in a specimen or a sample; in any case, the context of the descriptive material about an object will be set forth with clarity the meaning to be attached to the generic term "object" in that context.) The disclosure and teachings of the present invention address the problem of imaging an extended object that is embedded in a highly scattering medium. The kernel of the solution to the problem is the formulation of the aforementioned integral equation. Since diffusively transmitted light contains sufficient information for direct image reconstruction, the problem can be expressed in a tractable form amenable to an essentially closed-form solution—meaning that there is no need to rely upon or resort to an iterative/minimization-type reconstruction with all its shortcomings and pitfalls.

Figure 1:
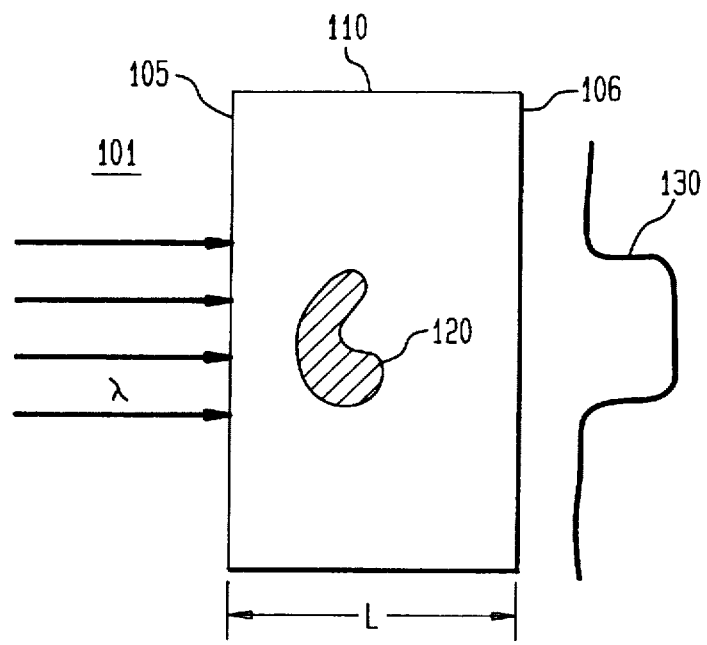
FIG. 1 depicts the transmission of light through a specimen containing an object in the ballistic limit.

For illustrative purposes, the case of only an absorbing object is considered. To elucidate the direct reconstruction process at its most fundamental level, a simplified system to which direct reconstruction is applicable is first described, namely, one in which a plane wave of light (photons) of wavelength $\lambda$ is incident upon a sample of linear dimension L that contains a spatially-extended object characterized by a position-dependent optical absorption coefficient; the width L is aligned with the impinging incident wave. If it is further assumed that photons are scattered by particles whose size is large compared to $\lambda$, then the scattering is described by a transport mean free path, designated l*; the mean free path characterizes the average distance a photon travels before its direction is randomized. In the single-scattering regime, that is, where l*>>L, it is observed that most of the incident wave is unscattered upon exiting the sample and thus may be used to form a projection image of the diffusing object; this effect is depicted in FIG. 1. In FIG. 1, light rays 101 of wavelength $\lambda$ impinge on front 105 of sample 110 containing diffusing object 120, wherein the light rays transmitted through sample 100 exiting back 106 of sample 110 form a projection image represented by trace 130. The transmitted intensity represented by trace 130 is related to the line integral of the optical absorption coefficient along the direction of propagation of the unscattered wave. This gives rise to the so-called Radon transform of the absorption coefficient. By inversion of the Radon transform, it is possible to recover the absorption coefficient and thus an image of diffuser 120 is reconstructed. As already alluded to above, all commercially available imaging techniques are based on this simple physical principle.

Figure 2:
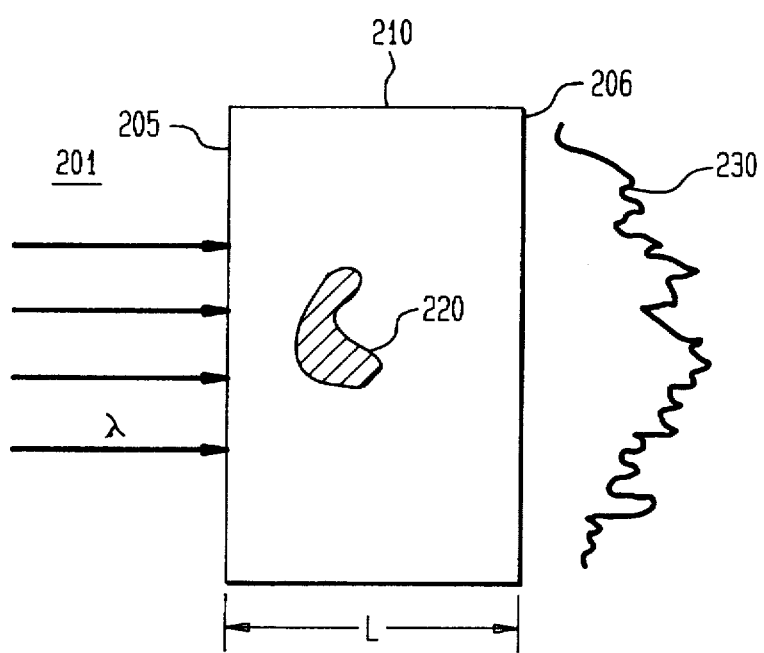
FIG. 2 depicts the transmission of light through a specimen containing an object in the diffusion limit.

In the multiple-scattering regime, that is, where l*<<L, a wave scatters many times while traversing the sample. In this situation, with $\lambda$<<l*, the path of a single photon may be described as a diffusive random walk where D=1/3(c/n)l* is a suitable diffusion constant, with c being the speed of light, n being the index of refraction, and c/n being the speed of light in the medium of the sample. The unscattered, or ballistic photons, are exponentially attenuated with a static transmission coefficient $T_{ball} \sim \exp(-L/l^*)$. The dominant contribution to the transmitted intensity is provided by diffusive photons with a diffusive transmission coefficient $T_{diff} \sim l^*/L$ which, even with coherent illumination, forms a complicated interference pattern that does not contain a simple image of the sample; such a pattern is illustrated in FIG. 2 (which has essentially the same pictorial representation as FIG. 1, except that the physical system of FIG. 2 is such that l*<<L as contrasted to l*>>L in FIG. 1). In FIG. 2, light rays 201 of wavelength $\lambda$ impinge on front 205 of sample 210 and eventually exit sample 210 from back 206. Absorbing object 220 gives rise to trace 230, which is representative of the complicated transmitted light pattern exiting back 206. In accordance with the present invention, there is devised a closed-form procedure for utilizing the information in such complicated patterns as exhibited by trace 230 to locate an object and thus perform optical imaging in the multiple-scattering regime.

Indeed, it has frequently been pointed out in the prior art that ballistic photons convey the least distorted image information while diffusive photons lose most of the image information. For this reason several elegant experimental techniques have been designed to select the ballistic photon contribution either by optical gating, holography, or filtering of the diffusive photons by optical diffusion. There is, however, an intrinsic physical limitation of any technique that relies solely on ballistic photons. This may be appreciated by considering the exponential attenuation of ballistic photons relative to the mild algebraic attenuation of diffusive photons. In particular, if the sample size L is sufficiently large compared to l*, then $T_{ball}$ will fall below an experimentally measurable threshold (e.g., if l* is about 0.5 millimeters, then the attenuation is proportional to $e^{-40}$ in only 2 centimeters).

Thus, the likelihood of now reconstructing important and valuable images heretofore believed to be virtually impossible to reconstruct provides a strong motivation to overcome the limitations of ballistic imaging by employing multiply scattered diffusive photons for image reconstruction. From fundamental physical principles, such a reconstruction from the interference pattern of diffusive transmitted light is attainable since such reconstruction is uniquely determined by two parameters, namely, the absorption and diffusion coefficients of the highly scattering system. The solution to this most general problem is, in a sense, a generalization of the Radon transform to diffusion imaging. As presented herein in accordance with the present invention, the diffusive transmission coefficient is related to the combination of an integral involving the absorption coefficient and another integral involving the diffusion coefficient. Then the image may be directly reconstructed using a suitable algorithm which references this combination of integral operators. In contrast to ballistic methods, the resulting reconstruction algorithm may be used to image samples whose size L is large compared to l*.

Function Theoretic Basis for Absorption and Diffusion Imaging

Figure 3:
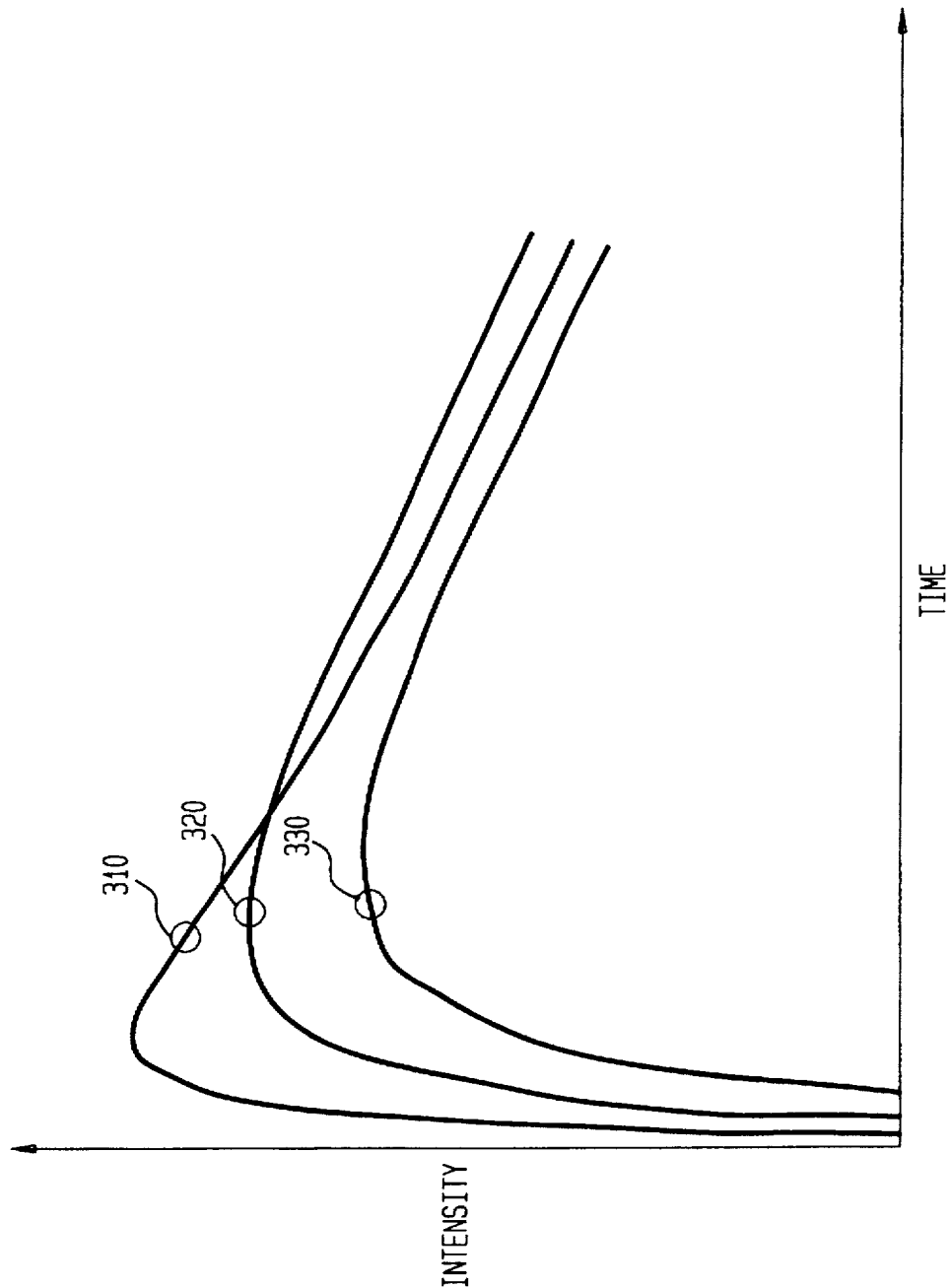
FIG. 3 illustrates the transmission of light through a specimen for several detector positions with a time-domain source.

The separation of ballistic and diffusive effects is most naturally effected with a time-resolved pulse propagation approach. In this approach, the time-dependence of the transmission coefficient of an optical pulse propagating in a highly scattering medium is observed. Transmission on short time scales is a measure of ballistic transport of photons in the single scattering regime. In contrast, transmission on long time scales (comparable to the diffusion time $\tau_D = L^2/D$) is a measure of diffusive transport in the multiple scattering regime; these short- and long-time scales are depicted in FIG. 3 for multiple detector locations. In FIG. 3, the transmission intensity of detected photons is shown quantitatively as the ordinate, with time displayed on the abscissa. A source-detector pair is positioned at three different locations proximate to a sample, such as shown in FIG. 2, with each location giving rise to a transmitted intensity versus time. Thus, for example, curve 310 corresponds to the first location of the source-detector pair, whereas curve 320 corresponds to the second location and, finally, curve 330 corresponds to the third location. It is noteworthy at this juncture to point out that all three curves have essentially the same slope after a long time interval.

Figure 4:
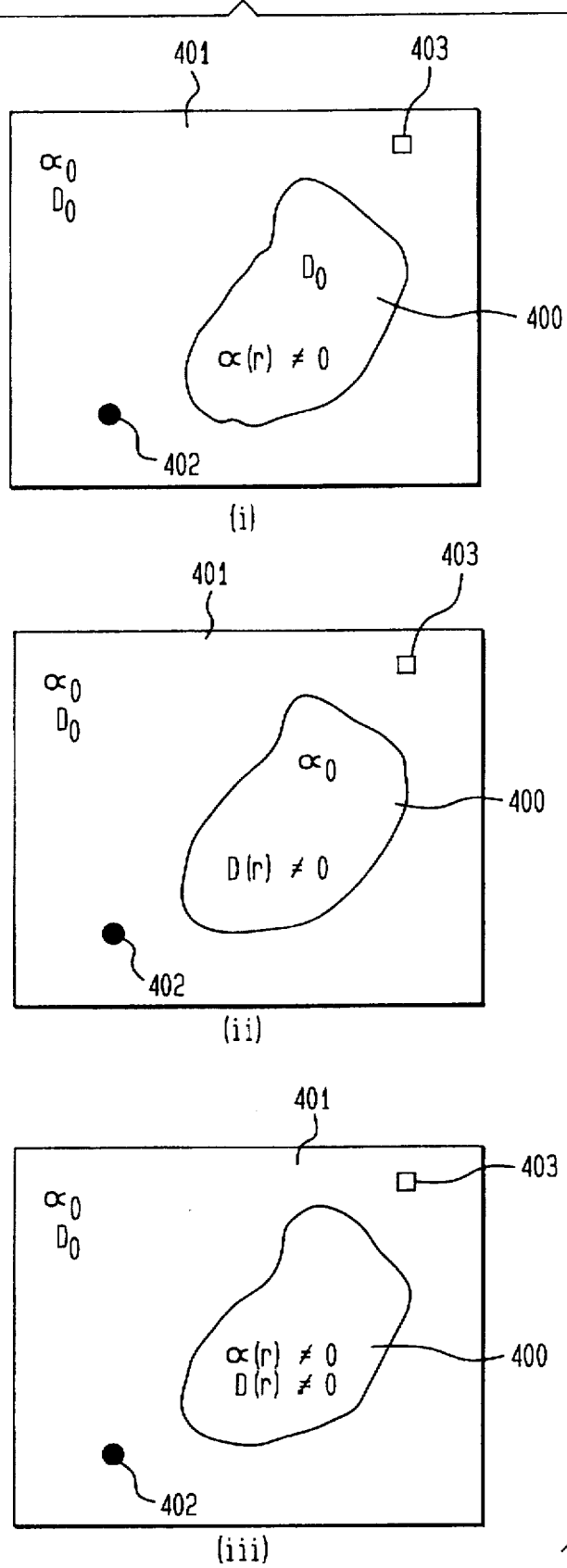
FIG. 4 depicts an object embedded in a medium for the cases of constant diffusion, constant absorption, and fluctuating diffusion and absorption, respectively.

The time-dependent diffusive intensity transmission coefficient $T(r_1,r_2,t)$ for a pulse propagating in time t from a source at $r_1$ to a detector $r_2$ is given by the following exponential law:

$$-\ln T(r_1,r_2,t) = \int d^3r \nu_A(r;r_1,r_2)\alpha(r) + \int d^3r \nu_D(r;r_1,r_2,t)D(r) \quad (1)$$

where $\alpha(r)$ is the fluctuation in absorption away from the background (designated $\alpha_0$), and D(r) is the fluctuation in diffusion away from the background (designated $D_0$). The diagram of FIG. 4 depicts these relations, namely, in FIG. 4(iii), object 400 is shown immersed in medium 401 which has absorption $\alpha_0$ and diffusion constant $D_0$; object 400, on the other hand, has absorption $\alpha(r) \neq 0$, and diffusion $D(r) \neq 0$. (Also shown for completeness is $i^{th}$ source 402 and $j^{th}$ detector 403 surrounding object 400, as discussed in detail shortly).

Equation (1) is valid in the limit of weak absorption or small spatial fluctuations in absorption and diffusion; if the medium is strongly absorbing the intensity of the transmitted light is negligible and imaging is not possible.

In equation (1), $\nu_A$ and $\nu_D$ are called the "absorption kernel" and "diffusion kernel", respectively, and are given by:

(1) Absorption Kernel $$\nu_A(r;r_1,r_2,t) = \frac{1}{G(r_1,r_2;t)} \int_0^t dt' G(r_1,r;t') G(r,r_2;t-t') \quad (2)$$

where $G(r_1,r_2;t)$ is the diffusion propagator that satisfies physically appropriate boundary conditions. An analytical expression for the absorption kernel in free space may be obtained with the result $$\nu_A(r;r_1,r_2,t) = \frac{1}{4\pi D} \left( \frac{1}{|r-r_1|} + \frac{1}{|r-r_2|} \right) \exp\left[ \frac{-1}{4Dt} ((|r-r_1|+|r-r_2|)^2 - (r_1-r_2)^2) \right]. \quad (3)$$

Figure 5:
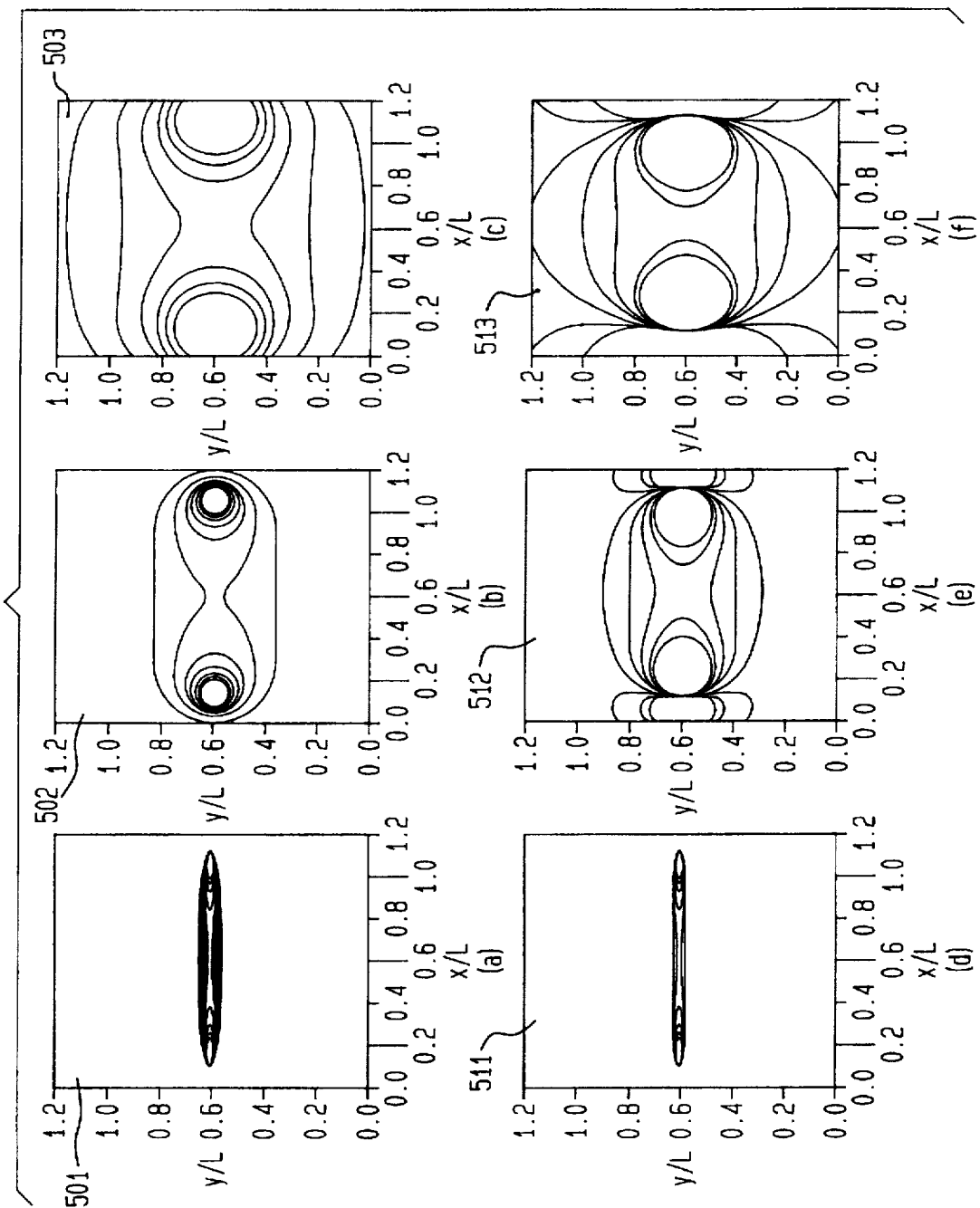
FIG. 5 depicts plots of the absorption kernel and the diffusion kernel for several time instants.

Contour plots of the absorption kernel are shown in FIG. 5(a)–(c) for various time instants corresponding to approximately 0.001 $\tau_D$, 0.1 $\tau_D$, and 1.0 $\tau_D$. As depicted, at very early times (FIG. 5(a)) the hitting density 501 is largely concentrated on the line connecting the source and detector. This represents the dominant contribution to the hitting density from nearly ballistic photons. At longer times (FIGS. 5(b) and 5(c)), in the multiple scattering regime, the hitting density (502 and 503, respectively) includes contributions from photons over longer paths.

(2) Diffusion Kernel $$\nu_D(r;r_1,r_2,t) = \quad (4)$$

$$\frac{1}{G(r_1,r_2;t)} \int_{0-}^t dt' \nabla_r G(r_1,r;t') \cdot \nabla_r G(r,r_2;t-t'),$$

where $G(r_1,r_2;t)$ is the diffusion propagator that satisfies physically appropriate boundary conditions. In free space, $$\nu_D(r;r_1,r_2,t) = \frac{Q}{4\pi D} \left( \frac{1}{|r-r_1|} + \frac{1}{|r-r_2|} \right) \exp\left[ \frac{-1}{4Dt} ((|r-r_1|+|r-r_2|)^2 - (r_1-r_2)^2) \right], \quad (5)$$

where $$Q = \frac{(r-r_1)(r-r_2)}{4(Dt)^2(r-r_1)^2(r-r_2)^2} [2Dt(|r-r_1|-|r-r_2|)^2 + |r-r_1||r-r_2|(2Dt + (|r-r_1|+|r-r_2|)^2].$$

Contour plots of the diffusion kernel are shown in FIG. 5(d)–(f) for various time instants corresponding to approximately 0.001 $\tau_D$, 0.1 $\tau_D$, and 1.0 $\tau_D$. As depicted, at very early times (FIG. 5(d)) the kernel 511 is largely concentrated on the line connecting the source and detector. This represents the dominant contribution to the kernel from nearly ballistic photons. At longer times (FIGS. 5(e) and 5(f)), in the multiple scattering regime, the kernel (512 and 513, respectively) includes contributions from photons over longer paths. Thus the kernels provide a physical picture of photon transport in the pulse propagation approach in the diffusion limit.

The integral equation (1) is referred to as the fundamental integral equation of photon diffusion imaging. It relates the transmission coefficient in the pulse propagation approach to both the absorption and the diffusion coefficients.

The central problem in photon diffusion imaging is the reconstruction of the image from transmission measurements for a family of source-detector pairs in a pulse propagation experiment. The description of a suitable reconstruction procedure requires the solution of the fundamental integral equation (1). This integral equation is a Fredholm equation of the first kind. Such equations are typically ill-posed and it is well-known that their solution requires the introduction of a regularization method. One approach to this problem is to consider a direct numerical implementation of the regularized singular value decomposition. Here the integral equation (1) is converted into a system of linear equations by an appropriate discretization method such as collocation with piecewise constant functions. This method requires that measurements of the transmission coefficient be obtained from multiple source-detector pairs; each pair contributes multiple time points as well. Thus at least as many source-detector pair/time point combinations are required as pixels in the reconstructed image. It is important to appreciate that the computational complexity of such a real-space reconstruction algorithm is o($N^3$) where N is the number of pixels in the reconstructed image. It is noted that this is simply the complexity of the associated numerical singular value decomposition.

Figure 6:
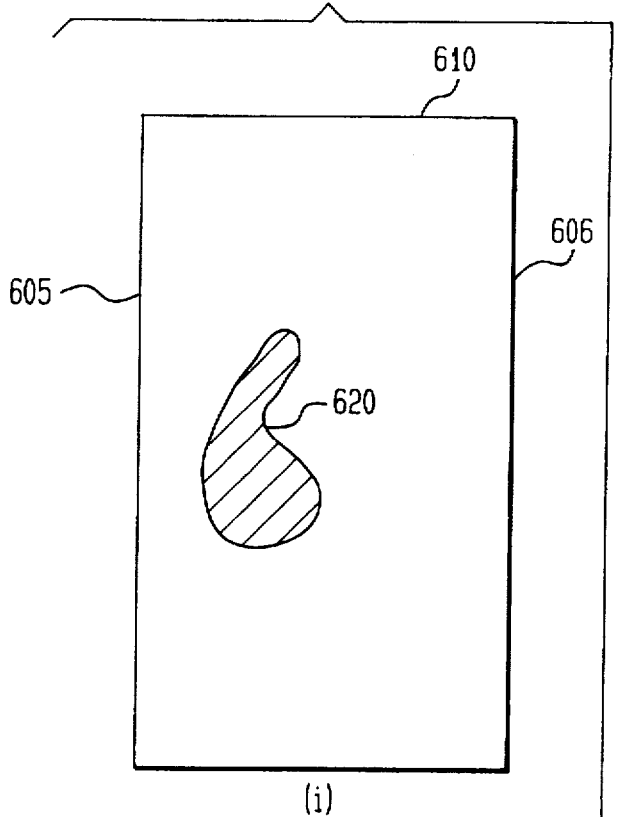
FIG. 6 illustrates an object in a specimen and a simulated reconstruction of the object using the direct reconstruction technique of the present invention.
Figure 6:
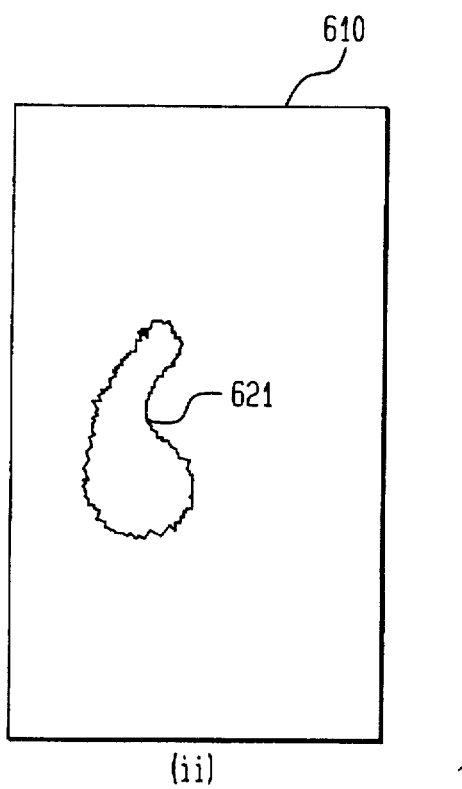

The direct reconstruction of a two-dimensional object using computer processing on simulated transmission data is shown in FIG. 6. In FIG. 6(i), object 620 is shown as embedded in sample 610. Since the shape of object 620 is known, it is possible to mathematically describe, and thereby to calculate the emanation of photons from back 606 due to photons impinging on front 605, that is, solve the so-called forward problem in diffusion imaging. Given the transmission intensity of photons detected proximate to back 606, the so-called inverse problem can be solved to directly reconstruct an image of object 620—such a directly reconstructed image is depicted by object 621 in FIG. 6(ii). It is important to emphasize that, although the transmission data is simulated, the algorithm used in the computer processing to reconstruct image 621 is the very one used to process actual measurements of transmission intensity detected from an actual sample. Such simulations afford the opportunity to study, for example, noise effects on the transmission intensity data and sensitivity of the reconstruction technique to the various locations of the source-detector pair.

Details of the Present Invention

I. SYSTEM

Figure 7:
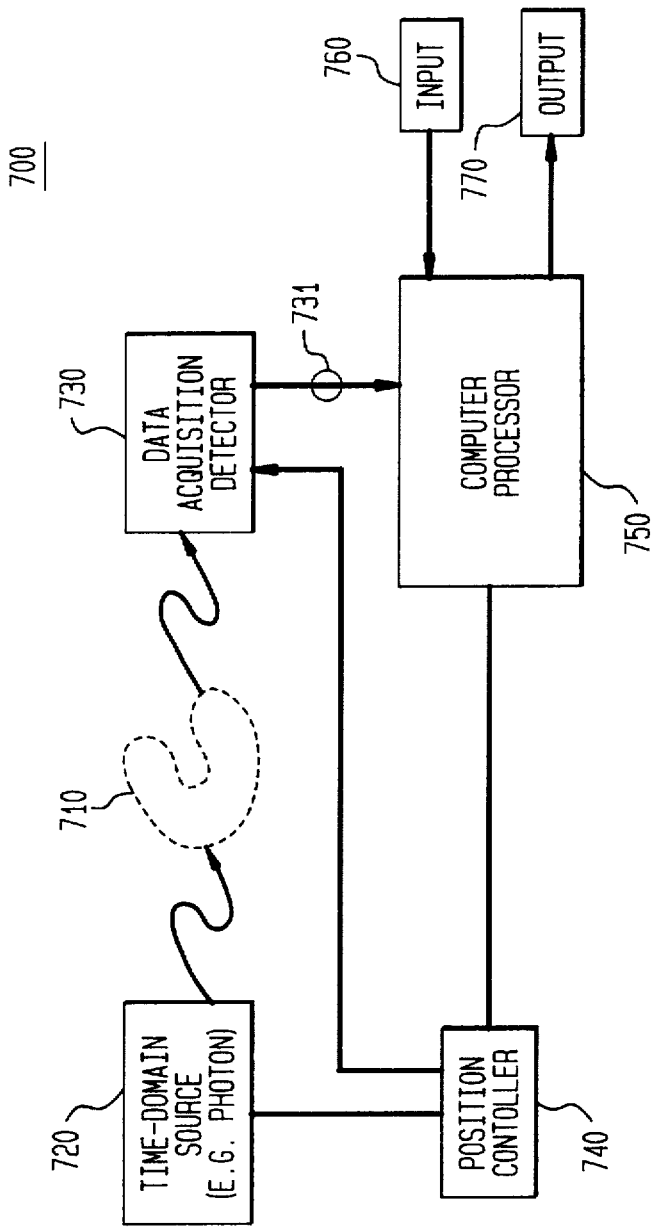
FIG. 7 illustrates a high-level block diagram one embodiment of the imaging system in accordance with the present invention.

As depicted in high-level block diagram form in FIG. 7, system 700 is a direct reconstruction imaging system for generating an image of an object using measurements of transmitted photons emanating from an object in response to photons impinging on the object. In particular, object 710 is shown as being under investigation. System 700 is composed of: time-domain source 720 for irradiating object 710 with photons; data acquisition detector 720 for measuring the transmitted intensity of photons emanating from object 710 at one or more strategic locations proximate to object 710; position controller 740 for controlling the location of detector 730 relative to time-domain source 720; and computer processor 750, having associated input device 760 (e.g. a keyboard) and output device 770 (e.g., a graphical display terminal). Computer processor 750 has as its inputs positional information from controller 740 and the measured transmitted intensity from detector 730.

In accordance with an illustrative embodiment of system 700, photon source 720 utilizes a tunable laser, Model MIRA-900P available from Coherent Corp. (This laser actually has two other auxiliary devices associated with it: (1) a acoustic-optic pulse picker to slow down the 78 MHz pulse rate to 5 Mhz—an exemplary device is Model 900 available from Coherent Corp.; and (2) another laser to pump the MIRA-900P—an exemplary pump laser is Model INNOVA-45 available from Coherent.)

Data acquisition detector 730 utilizes a photon detector exemplified by a streak-scope Model 64-334-02 available from Hamamatsu Corp.

Position controller 740 is utilized whenever photon source 720 and/or data acquisition detector 730 may be composed of a plurality of lasers or photon detectors in order to control which of the plurality of lasers may be energized for a given time period and which of the plurality of photon detectors may be activated during a prescribed time interval. As will be discussed in more detail below, in a practical implementation of the direct reconstruction imaging technique, it is oftentimes necessary to measure the transmitted photon intensity effected by a number of source-detector positions surrounding object 710. For the sake of expediency, generation of the required transmitted intensity data is expeditiously accomplished by having arrays of P laser sources and Q photon detectors. Accordingly, photon source 720 may be composed, in its most general implementation, of P laser sources or the like arranged strategically around the periphery of object 710. Similarly, data acquisition detector may be composed, in its most general realization, of Q photon detectors or the like also arranged strategically around the periphery of object 710 and in a cooperative relation with the P sources.

Computer 750 stores a computer program which implements the direct reconstruction algorithm; in particular, the stored program processes the measured transmitted data to produce the image of the object under study using a prescribed mathematical algorithm which references an integral operator—the integral operator involves both the absorption coefficient $\alpha(r)$ and the diffusion coefficient $D(r)$. The processing effected by computer 750 is the focus of the discussion of the methodology section of this description, which follows immediately.

II. METHODOLOGY

Computational Model

The fundamental integral equation expressed by equation (1), repeated here, $$-\ln T(r_1,r_2,t) = \int d^3r \nu_A(r;r_1,r_2)\alpha(r) + \int d^3r \nu_D(r;r_1,r_2,t)D(r) \quad (1)$$

is in the form of a Fredholm equation of the first kind (specifically referred to herein as the Schotland Third Time-Domain Integral Equation). In general, equation (1) holds for each set of measurements made with pre-determined source and detector positions; for a first set of measurements, equation (1) has the following form:

$$\int K_{11}(r,r')f_1(r')d^3r' + \int K_{12}(r,r')f_2(r')d^3r' = g_1(r); \quad (6)$$

similarly, for a second set of measurements, the following obtains:

$$\int K_{21}(r,r')f_1(r')d^3r' + \int K_{22}(r,r')f_2(r')d^3r' = g_2(r); \quad (7)$$

Relations (6) and (7) may be summarized in the general form $$Kf=g \quad (8)$$

where K is a matrix of integral operators and f,g are vectors of elements in appropriately selected function spaces. Equation (8) is said to be ill-posed if (a) it is not solvable, (b) a unique solution does not exist, or (c) the solution does not depend continuously on the data. The latter case (c) is of primary interest in the numerical study of ill-posed problems because it may lead to numerical instability. This is particularly important if the data is imprecisely known or is the subject to statistical uncertainties, such as measurement inaccuracy or noise, which would be the situation for measurements for imaging. There are methods for conditioning ill-posed problems. First, if the solution does not exist, the minimizer of $\|Kf-g\|$ is defined as a solution. Non-uniqueness is handled by choosing the minimizer with the least norm. Finally, continuity is restored by introducing "regularization" to the solution procedure.

Solving for the minimizer with the least norm yields the "normal equation" relating to equation (8); the normal equation is of the form $$K^*Kf = K^*g, \quad (9)$$

where $K^*$ is the adjoint of K, and the property that $K^*K$ is self-adjoint has been employed. Thus, a solution for f in equation (8) is of the following form:

$$f=(K^*K)^{-1}K^*g=K^+g. \quad (10)$$

From equation (10), $$K^+=(K^*K)^{-1}K^* \quad (11)$$

is called the "generalized inverse" of K.

Singular Value Decomposition

If K is such that a mapping from $H_1$ to $H_2$ occurs, where $H_1$ and $H_2$ are Hilbert spaces, then $K^*K$ is a self-adjoint, positive operator. If the eigenfunctions and eigenvalues of $K^*K$ are denoted by $\{f_n\}$ and $\{\sigma_n^2\}$, respectively, then the following relation obtains:

$$K^*Kf_n=\sigma_n^2 f_n. \quad (11)$$

The $\{\sigma_n\}$ are the singular values of K. Also, the $\{f_n\}$ form a basis for $H_1$. The singular values are ordered as $\sigma_1^2 \geq \sigma_2^2 \geq \ldots \geq 0$, where multiplicities are counted and 0 can appear with infinite multiplicity.

If $\{g_n\}$ is defined by $$Kf_n=\sigma_n g_n, \quad (12)$$

then the $\{g_n\}$ are a basis for Hilbert space $H_2$. Moreover, it then follows that $$K^*g_n=\sigma_n f_n. \quad (13)$$

To derive the singular value decomposition of K, put K in the form $$K=I_{H_2}KI_{H_1} \quad (14)$$

and use the identities $$I_{H_1}=\sum_n f_n \otimes f_n \quad (15)$$

and $$I_{H_2}=\sum_n g_n \otimes g_n. \quad (16)$$

where $\otimes$ denotes the tensor product. Manipulation of equations (14)–(16) leads to $$K = \sum_n \sigma_n g_n \otimes f_n. \quad (17)$$

Equation (17) is called the "singular value decomposition" of K.

The singular value decomposition of equation (17) can now be used to obtain a form for the generalized inverse $K^+$ of equation (11). As a result of equation (17), $$K^*K = \sum_n \sigma_n^2 f_n \otimes f_n \quad (18)$$

and $$K^* = \sum_n \sigma_n f_n \otimes g_n. \quad (19)$$

then it directly follows, after substitution of equations (18) and (19) into equation (11), that $$K^+ = \sum_n \frac{1}{\sigma_n} f_n \otimes g_n. \quad (20)$$

Now, using equations (10) and (20), the solution of Kf=g is $f=K^+g$, which is of the form $$f = \sum_n \frac{1}{\sigma_n} <g_n, g> f_n. \quad (21)$$

If some of the $\sigma_n$'s vanish, then $K^+$ is not well-defined and, in particular, is not continuous. To resolve this anomaly, the regularization procedure is introduced.

Regularization

To condition the singular value decomposition, the following expression is now defined:

$$K_\beta^+ = \sum_n R_\beta(\sigma_n) f_n \otimes g_n. \quad (22)$$

where the regularizer $R_\beta(\sigma)$ has the properties (i) $R_\beta(\sigma)=1/\sigma$ as $\beta \to 0^+$;

(ii) $R_\beta(\sigma) \sim 1/\sigma$ for $\sigma \gg 0$ (with $\beta > 0$); \quad (23)

(iii) $R_\beta(\sigma) \to 0$ as $\sigma \to 0$ (with $\beta > 0$).

For instance, two natural choices (others are possible) include:

(a) $R_\beta(\sigma)=1/\sigma$ for $\sigma > \beta$; otherwise, $R_\beta(\sigma)=0$; \quad (24)

(b) $R_\beta(\sigma)=\sigma/(\beta+\sigma^2)$. \quad (25)

(One typical heuristic criterion is to set $\beta \sim o(\sigma_1)$).

Thus the solution of equation (8) may be written as $$f(r)=\int d^3r' K_\beta^+(r,r')g(r') \quad (26)$$

where $$K_\beta^+(r, r') = \sum_n R_\beta(\sigma_n) f_n(r) g_n(r'). \quad (27)$$

(The form of equation (7) follows from the generic notation used to obtain equation (27)).

Numerical Solution of the Schotland's Third Equation

The above developments for the formal solution of a general Fredholm equation of the first kind, including the techniques of singular value decomposition and regularization, may now be applied to implement the numerical solution of equation (1):

$$-\ln T(r_1, r_2, t) = \int d^3 r \nu_A(r; r_1, r_2) \alpha(r) + \int d^3 r \nu_D(r; r_1, r_2, t) D(r). \quad (1)$$

For a three-dimensional object, denoted $\Omega$, it is supposed that there are P sources and Q detectors used to probe the object. These sources are spaced about the periphery of the object and, operating in conjunction with the sources, there are suitably placed detectors. For the sake of simplicity, a single time point is considered in the following exposition. In general, the results may be readily extended to the case of multiple time points. Let i, i=1,2, ... ,P and j, j=1,2, ... ,Q be indices corresponding to the P sources and Q detectors; then, for a given time, equation (1) becomes:

$$-\ln T_{ij} = \int_\Omega d^3 r (\nu_A')_{ij}(r) \alpha(r) + \int_\Omega d^3 r (\nu_D')_{ij}(r) D(r). \quad (28)$$

Now $\nu_A$, $\nu_D$, $\alpha(r)$ and $D(r)$ are discretized by decomposing $\Omega$ into "boxels" (i.e., volume elements having basically equal sides) $C_m$, m=1,2, ... ,M which cover the object. It is then assumed that the granularity is such that $\alpha(r)$, $D(r)$, $\nu_A$ and $\nu_D$ are constant in each box. To recast equation (28) in a standard form, the following identifications are made:

$$|C_m|(\nu_A')_{ij}(r_m) \equiv A_{ij}^m, \quad (29)$$

$$|C_m|(\nu_D')_{ij}(r_m) \equiv B_{ij}^m, \quad (30)$$

$$\alpha(r_m) \equiv a_m, \quad D(r_m) \equiv b_m, \quad (31)$$

and $$-\ln T_{ij} \equiv c_{ij}, \quad (32)$$

where $|C_m|$ is the volume of a boxel, $a_m$ is the strength of $\alpha(r_m)$ at the middle of the $m^{th}$ boxel, and $b_m$ is the strength of $D(r_m)$ at the middle of the $m^{th}$ boxel. Then, using these definitions, equation (28) becomes $$\sum_m A_{ij}^m a_m + \sum_m B_{ij}^m b_m = c_{ij}. \quad (33)$$

for m=1,2, ... ,M; i=1,2, ... ,P; and j=1,2, ... ,Q.

For instance, to illustrate equation (33) in long form, without loss of generality, let P=Q=2 and M=3:

$$A_{11}^1 a_1 + A_{11}^2 a_2 + A_{11}^3 a_3 + B_{11}^1 b_1 + B_{11}^2 b_2 + B_{11}^3 b_3 = c_{11} \quad (34a)$$

$$A_{12}^1 a_1 + A_{12}^2 a_2 + A_{12}^3 a_3 + B_{12}^1 b_1 + B_{12}^2 b_2 + B_{12}^3 b_3 = c_{12} \quad (34b)$$

$$A_{13}^1 a_1 + A_{13}^2 a_2 + A_{13}^3 a_3 + B_{13}^1 b_1 + B_{13}^2 b_2 + B_{13}^3 b_3 = c_{13} \quad (34c)$$

$$A_{14}^1 a_1 + A_{14}^2 a_2 + A_{14}^3 a_3 + B_{14}^1 b_1 + B_{14}^2 b_2 + B_{14}^3 b_3 = c_{14} \quad (34d)$$

(The above set of four equations, referred to as equation (34), is presented merely for illustrative purposes since it should be noted that set (34) has four equations and six unknowns, that is, the set is "underdetermined". However, it is possible to generate additional equations so as to "overdetermine" the system, as now discussed.) The above set of four equations may be written as Sx=c, where x is a column vector expressed as follows:

$$x = \begin{pmatrix} a_1 \\ a_2 \\ a_3 \\ b_1 \\ b_2 \\ b_3 \end{pmatrix}$$

and S is the matrix of coefficients appropriate to equation (34). Accordingly, the matrix form of equation (33) is represented as Sx=c, where S is a (PQ by 2M) matrix, that is, equation (33) yields PQ equations in 2M unknowns. It is preferable to "overdetermine" equation (33) by having PQ>2M, or by using multiple time points for each source-detector pair. If there are K time points, then matrix S is (KPQ by 2M) matrix. Typically in practice KPQ=6M.

The solution of singular value decomposition applied to a matrix formulation is a well-known technique. For example, a procedure for singular value decomposition is described in the text "Numerical Recipes", by Press, Flannery, Teukolsky, and Vettering, 1986, Cambridge University Press, Cambridge, England. A commercially available software package implementing the singular value decomposition, called Interactive Data Language (IDL) available from Research Systems Inc. of Denver, Colo., may be used in practice; IDL was specifically designed for scientific computations, especially image processing applications. With IDL, a subroutine-like call of the form "SVD [Matrix]" (e.g. SVD [S]) in terms of the above S matrix returns the singular values which may then be used to solve the system of linear equations.

Once the singular value decomposition has been effected, regularization according to equation (27) is readily accomplished in order to obtain the regularized, generalized inverse for the matrix S, which is denoted $S^+$. The solution to the discretized Schotland's Third Integral Equation becomes $x = S^+ c$.

FLOW DIAGRAMS

Figure 8:
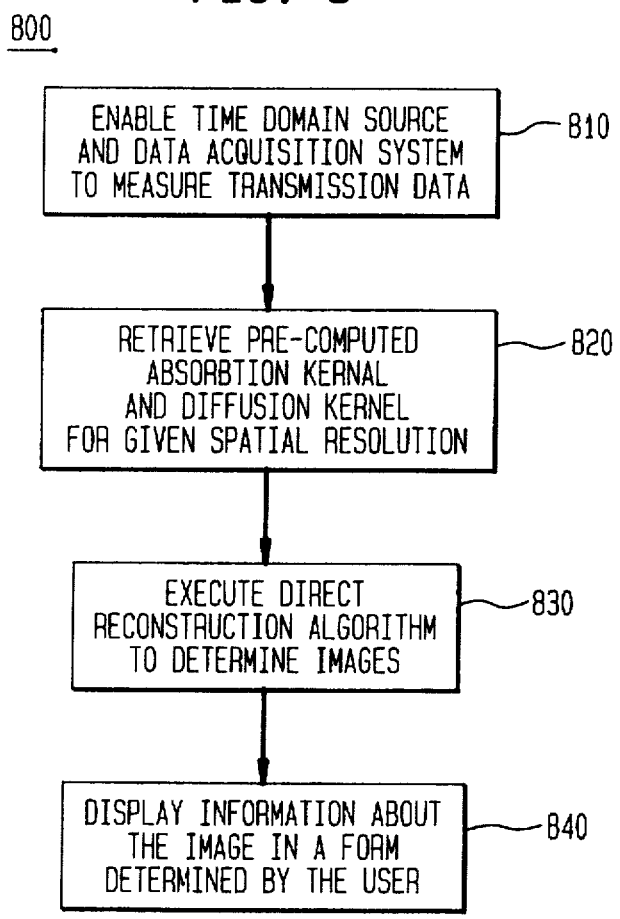
FIG. 8 is a high-level flow diagram of the methodology of the present invention.

The methodology discussed in the previous section is set forth in high-level flow diagram 800 in FIG. 8 in terms of the illustrative embodiment of the system shown in FIG. 7. With reference to FIG. 8, the processing effected by control block 810 enables time-domain photon source 720 and data acquisition system 730 so as to measure energy emanating from object 710 due to photon source 720. These measurements are passed to computer processor 750 from acquisition system 730 via bus 731. Next, processing block 820 is invoked to retrieve the pre-computed and stored absorption and diffusion kernels. In turn, processing block 830 is operated to execute the direct reconstruction algorithm set forth with respect to equations (8)–(33), thereby determining the absorption coefficient $\alpha(r)$ and the diffusion coefficient D(r). Finally, as depicted by processing block 840, the reconstructed images corresponding to the absorption coefficient $\alpha(r)$ and the diffusion coefficient D(r) are provided to output device 770 in a form determined by the user; device 770 may be, for example, a display monitor or a more sophisticated three-dimensional video display device.

Figure 9:
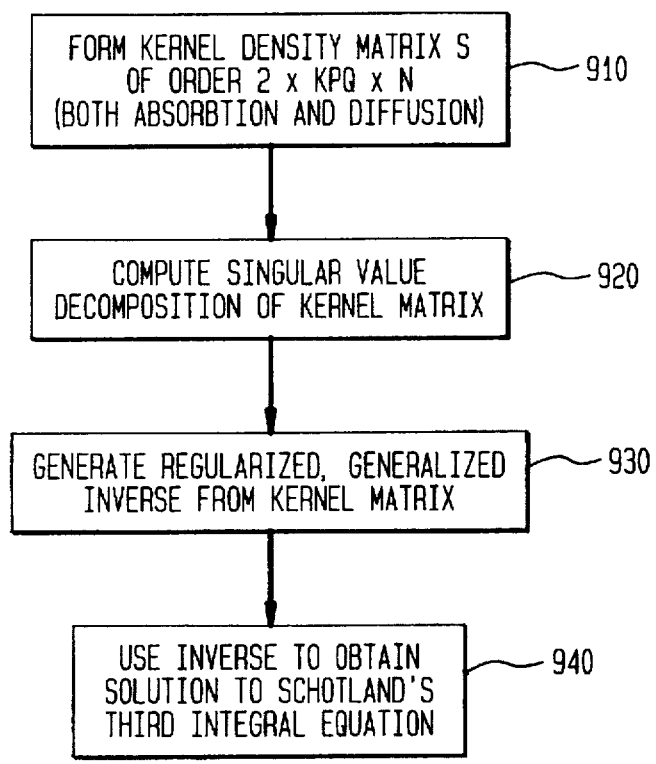
FIG. 9 is a flow diagram depicting one methodology for computing the diffusion of the object under investigation.
Figure 10A:
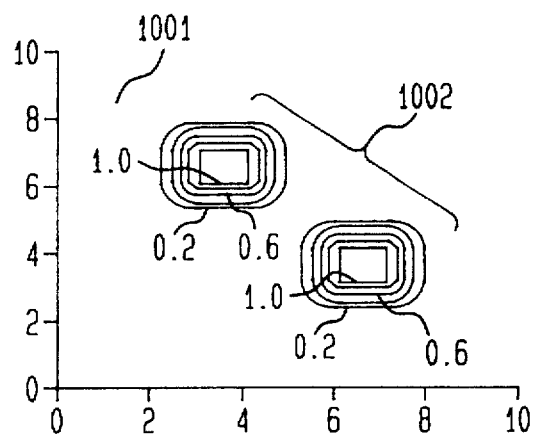
FIG. 10 shows a reconstructed exemplary object.
Figure 10B:
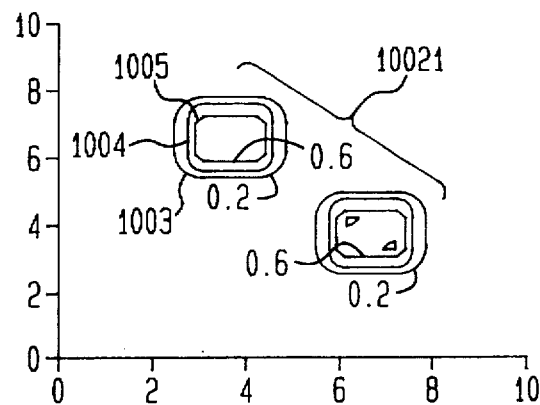
Figure 10C:
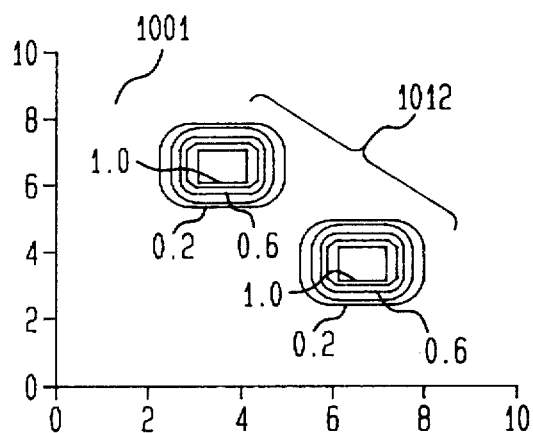
Figure 10D:
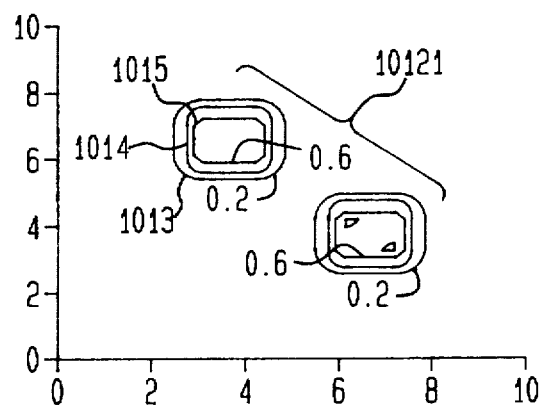

One illustrative manner of carrying out the direct reconstruction exhibited by block 820 is further depicted by high-level flow diagram 900 of FIG. 9. In particular, processing block 910 shows that the first step is to form the kernel matrix S as determined by discretization, that is, S is formed from $A_{ij}^m$ for m=1,2, . . . , M; i=1,2, . . . ,P; j=1,2, . . . ,Q, and $B_{ij}^m$ for m=1,2, . . . , M; i=1,2, . . . ,P; j=1,2, . . . ,Q, respectively. Next, processing block 920 is invoked to compute the singular value decomposition of the kernel matrix S. Then, processing block 930 is executed to generate the regularized, generalized inverse $S^+$. Finally, block 940 is invoked to obtain the solution x=S+c.

With reference to FIG. 10, there is shown the direct reconstruction of an exemplary object. In particular, FIG. 10(a) shows the direct reconstruction of the absorption image 1002 of a two-dimensional object embedded in a 10 cm×10 cm specimen 1001. FIG. 10(b) shows the direct reconstruction of the absorption image 10021 in the presence of additive Gaussian noise of 0.1% to indicate the relative insensitivity of the direct reconstruction to noise. FIG. 10(c) shows the direct reconstruction of the diffusion image 1012 of a two-dimensional object embedded in a 10 cm×10 cm specimen 1001. FIG. 10(d) shows the direct reconstruction of the diffusion image 10121 in the presence of additive Gaussian noise of 0.1% to indicate the relative insensitivity of the direct reconstruction to noise. In this example, $\alpha_0=1.0$ cm$^{-1}$ and $D_0=1.0$ cm$^2$ns$^{-1}$ and the contour levels 1003, 1004, 1005, and 1013, 1014, and 1015 refer to fluctuation in the absorption coefficient measured in units of cm$^{-1}$ and diffusion coefficient in units of cm$^2$ns$^{-1}$, respectively. The transmission coefficients were obtained using Monte Carlo simulations.

The system and methodology described utilizes the free-space model of the absorption and diffusion kernels so that the absorption and diffusion kernels are pre-computed and stored in computer processor 750 for recall during the reconstruction process. This is appropriate when object 710 is surrounded by an arrangement, such as a thin, rubber-like container filled with a substance (e.g., the commercially available medical product called Intralipid), so that the arrangement provides a spatial extent external to the object that effectively gives rise to a free-space condition surrounding the object. The object's actual boundary (e.g., a human skull during imaging of brain) becomes merely another shape that is determined by the direct reconstruction procedure. Intralipid is useful because it is a colloidal substance wherein particles in the range of 0.5 microns to 2 microns are suspended, and the substance, as packaged, does not rapidly deteriorate; moreover, the l* of such a substance is readily measurable.

It is to be understood that the above-described embodiment is simply illustrative of the application of the principles in accordance with the present invention. Other embodiments may be readily devised by those skilled in the art which may embody the principles in spirit and scope. Thus, it is to be further understood that the methodology described herein is not limited to the specific forms shown by way of illustration, but may assume other embodiments limited only by the scope of the appended claims.

What is claimed is:

1. A method for generating absorption and diffusion images of an object comprising the steps of irradiating the object with a time-domain source of radiation, measuring a transmitted intensity due predominantly to diffusively scattered radiation wherein said transmitted intensity is related to an absorption coefficient and a diffusion coefficient by an integral operator, and directly reconstructing the images by executing a prescribed mathematical algorithm, determined with reference to said integral operator, on said transmitted intensity, said step of directly reconstructing including the step of computing an absorption kernel and a diffusion kernel.

2. The method as recited in claim 1 wherein the step of irradiating the object includes the step of successively irradiating the object with different wavelengths.

3. A system for generating absorption and diffusion images of an object comprising time-domain radiation source means for irradiating the object, detector means for measuring a transmitted intensity due predominantly to diffusively scattered radiation wherein said transmitted intensity is related to an absorption coefficient and a diffusion coefficient by an integral operator, and means for directly reconstructing the images by executing a prescribed mathematical algorithm, determined with reference to said integral operator, on said transmitted intensity, said means for directly reconstructing including means for computing an absorption kernel and a diffusion kernel.

4. The system as recited in claim 3 wherein said source means for irradiating the object includes means for successively irradiating the object with different wavelengths.

* * * * *